United States Patent [19]
Olim

[11] Patent Number: 4,853,974
[45] Date of Patent: Aug. 8, 1989

[54] FRAMELESS FACE PROTECTOR

[76] Inventor: Marvin J. Olim, 20735 Castle Bend, Katy, Tex. 77450

[21] Appl. No.: 163,671

[22] Filed: Mar. 3, 1988

[51] Int. Cl.$^4$ ............................ A61F 9/04; A61F 9/06
[52] U.S. Cl. ................................................ 2/9; 2/206
[58] Field of Search .......... 2/9, 11, 174, 206, DIG. 11

[56] References Cited

U.S. PATENT DOCUMENTS

| | | | |
|---|---|---|---|
| 1,911,817 | 5/1933 | DuBois | 2/9 |
| 2,881,443 | 4/1959 | Barker, Jr. | 2/9 |
| 4,630,317 | 12/1986 | Brown et al. | 2/DIG. 11 |
| 4,686,690 | 8/1972 | Webb | 2/9 |

*Primary Examiner*—Werner H. Schroeder
*Assistant Examiner*—Jeanette E. Chapman
*Attorney, Agent, or Firm*—Michael P. Breston

[57] ABSTRACT

The face protector comprises a flexible headband and a transparent flexible shield of sufficient size to protect the face of the wearer. The shield is sufficiently flexible and easily deformable so as to adapt to the shape of a user's head. Fastener means carried by the headband reusably and deftly attaching the band around the head of the wearer and also reusably and deftly attaching the headband to the shield. The fastener means on the headband are attached to lateral positions on the headband, and the fastener means on the shield are detachably suspended from the fastener means on the headband at these positions.

4 Claims, 1 Drawing Sheet

FRAMELESS FACE PROTECTOR

FIELD OF THE INVENTION

The invention relates in general to face protectors and, more particularly, to dental and medical face protectors.

BACKGROUND OF THE INVENTION

Face protectors are now widely used by dentists, medical practitioners, and their auxiliary personnel in order to reduce the risk of direct facial contact with airborne micro organisms, minute particulate matter and liquid matter, and to gain protection against hazardous particles and contagious diseases.

The prior art face protectors use a variety of frames which support their shields with screws, bolts or clamps. The known face protectors are characterized by one or more of the following drawbacks: they are cumbersome and unsightly; they are stifling to wear and clumsy to place on and remove from the head of the wearer; their frames tend to mess up the operators' hair; they create pressure points on the head and face and consequential headaches; they are awkward to sanitize; their shield, due to its bulk and rigidity, pokes the patient, operator, and/or tools; they lack proper air circulation, and are subject to moisture accumulation and fogging.

It will be appreciated that using such prior art face protectors, especially in a 8-hour day practice, becomes disruptive to the dentist, his staff, as well as to patients.

Therefore, there is a great need for a very simple face protector which is safe, substantially trouble-free, and inexpensive to purchase so that it can be disposed, if necessary, without imposing an appreciable financial burden.

Accordingly, it is a main object of this invention to provide a new and unique approach to solving the above and other known face protector problems which, although heretofore recognized, have not been effectively addressed in this field.

It is a specific object to provide a face protector which requires no frame, and which uses Velcro (TM of Velcro USA, Inc.) type fasteners.

SUMMARY OF THE INVENTION

The face protector comprises a flexible headband and a transparent flexible shield of sufficient size to protect the face of the wearer. The shield is sufficiently flexible and easily deformable to match the shape of the user's head. Fastener means carried by the headband and by the shield reusably fasten the band around the head of the wearer and also reusably fasten the shield to the headband. The fastener means are deformable to match the shape of the headband and to match the shape of the shield.

The shield is suspended from the headband so as to establish a sufficient anterior opening between the headband and the shield to allow for adequate and unobstructed air circulation through the opening to and from the nostrils of the wearer along the posterior side of the shield.

In a preferred embodiment the shield is made of a lightweight transparent plastic material having a thickness from 0.007" to 0.016". The fastener means operate in pairs, one being a woven strip carrying woven hooks, and the other being a woven strip carrying woven loops to allow for detachable mechanical interaction to take place between the hooks and the loops.

DESCRIPTION OF A PREFERRED EMBODIMENT

Figure 1:
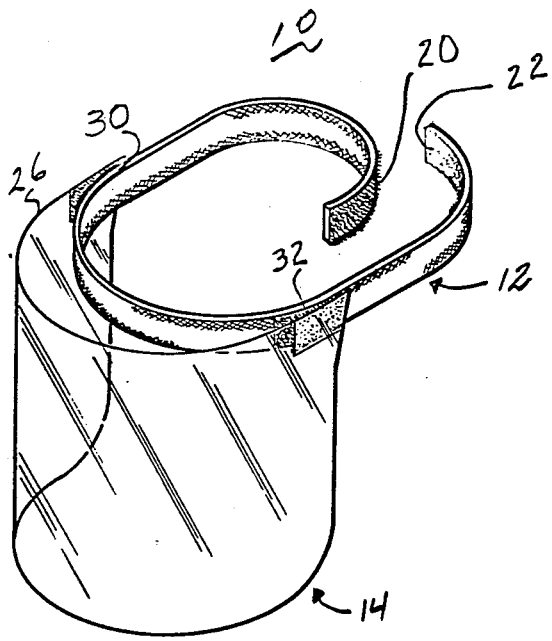
FIG. 1 is a perspective view of the novel face protector shown in assembled form.
Figure 2:
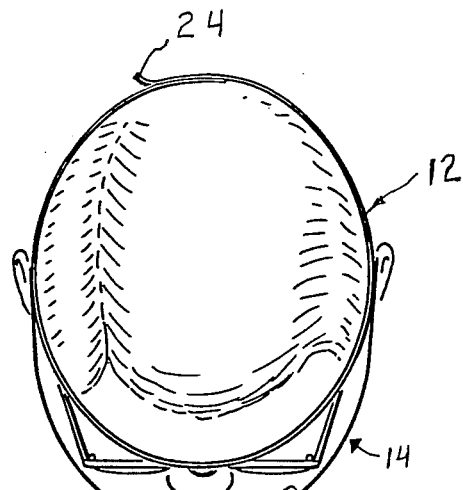
FIG. 2 is a top view of the face protector on a user's head.
Figure 3:
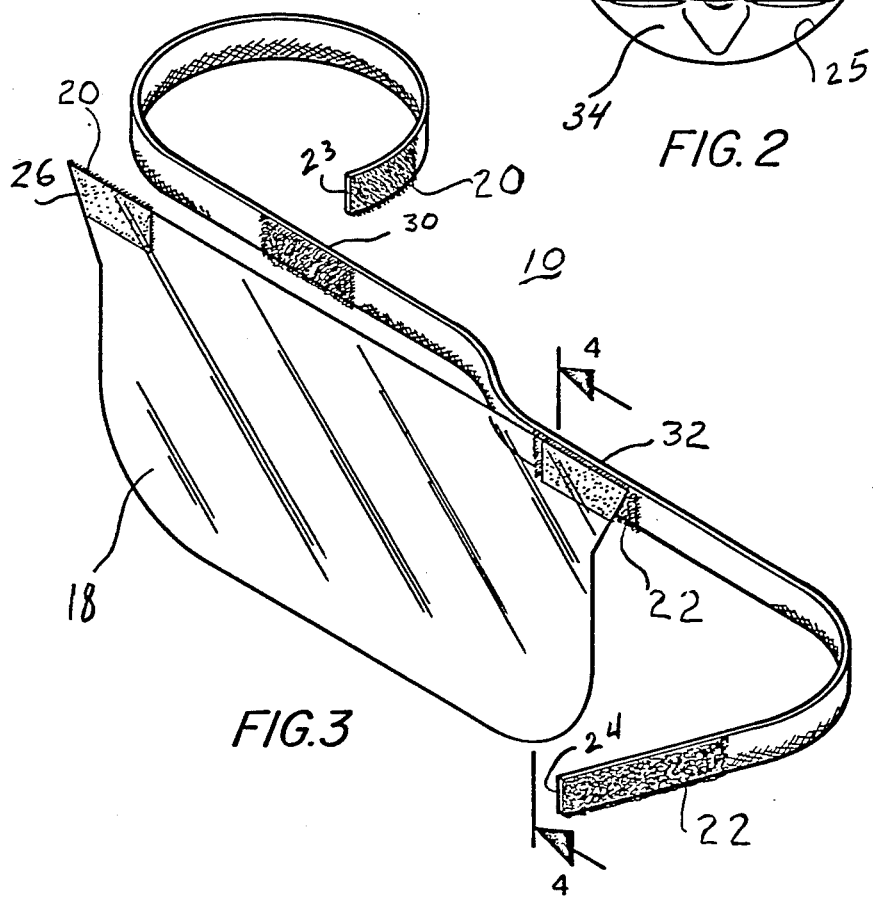
FIG. 3 is a perspective view of the face protector shown in partially disassembled form.
Figure 4:
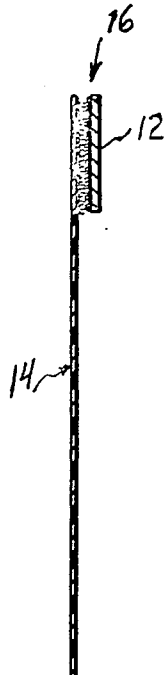
FIG. 4 is a sectional view on line 4—4 of FIG. 3.

The novel face protector of this invention, generally designated as 10, requires no frame and can be used indoor and outdoor in dental, medical, and other such hazardous environments.

Face protector 10 comprises a flat headband 12, a flat shield 14, and a flat fastener means 16, all interacting when properly interconnected to produce the synergistic result of the invention.

Headband 12 is designed to have the following mechanical and functional properties: it is reusable, inexpensive, perspiration absorbent, sufficiently strong to carry the light weight of shield 14, and sufficiently wide to transmit substantially uniformly the load from shield 14 to the head of the user, thereby preventing concentrated zones of pressure which might otherwise lead to pain, headaches, and/or marks upon the face. Headband 12 does not mess the operator's hair, and can be donned and removed quickly.

To accomplish these objectives, headband 12 is preferably of a suitable deformable ribbon made of one inch wide absorbent material such as cotton, woven polyester, nylon, or similar material.

Shield 14 is designed to have the following mechanical and functional properties: it is reusable, inexpensive, has adequate thickness for sufficient strength yet is thin enough to be flexible and easily deformable in order to match the shape of the user's head and to deflect upon accidental contact with the operator, his instruments and/or patient; it is easily trimmable with knife or scissors; it is resistant to weather, water, and common dental chemicals; it is compatible with sanitary procedures; it accepts adhesive bonding to fastener means 16; and it has good transparency.

Shield 14 has an anterior surface 18 of sufficient size to protect the entire face of the wearer. It is made of a lightweight transparent plastic material having a thickness from 0.005" to 0.025" and a preferred range from 0.007" to 0.016" for optimum flexibility.

Fastener means 16 has the following mechanical and functional properties: it is inexpensive and sufficiently strong to resist the shear and tensile forces from shield 14, and yet is thin enough to remain flexible and easily deformable in order to match the shape of the wearer's head; it is resistant to weather, water, and ordinary chemicals; it can be made compatible with sanitary procedures; it is able to accept adhesive bonding to band 12 and to shield 14 or it can be sewn for greater permanence and washability of band 12; it deftly unfastens without messing up the hair of the wearer, by applying a light tensile force with two fingers for quick and easy shield and band removal, and it can be deftly refastened by exerting light pressure; it acts as a shock absorber between shield 14 and band 12; and it allows band 12 to accommodate different size shields 14, different shield positions, different air circulation patterns, and different head sizes.

To accomplish these objectives, fastener means 16 preferably includes ¾" wide Velcro hook and loop strips 20,22, respectively, in order to obtain an extensive surface contact with shield 14 and headband 12.

The operation of strips 20,22 depends on the engagement between many woven monofilament hooks on strip 20 with woven loop filaments on the apposite strip 22. Strips 20,22 are durable and can be attached and detached many thousands of times. All that is necessary to separate strips 20,22 is to peel one strip from the other.

Strips 20,22 provide an adjustable self-locking action to opposite ends 23,24 of band 12 so that it can snugly fit around the wearer's head.

Strips 20,22 are also used to fasten shield 14 at two or more positions on band 12.

For that purpose hook strips 20 are bonded below the top edge 26 to the posterior side 25 of shield 14 and near the corners 27,28 thereof. Such bonding to shield 14 can be effected by a suitable adhesive.

The mating loop strips 22 are bonded or sewn to the lateral positions 30,32 on band 12. The loop strips 22 on band 12 become detachably fastened to the hook strips 20 on shield 12 in whatever position they are pressed together.

The mounting of shield 14 on band 12 is achieved at positions 30,32 in such a manner that an anterior opening 34 becomes established between band 12 and top edge 26 of shield 14.

An additional mounting position (not shown) on band 12 can be selected half-way between positions 30,32. In this position, two openings would be formed between band 12 and top edge 26 of shield 14.

Such mountings of shield 14 on band 12 are compatible with wearing eye glasses and with providing an unobstructed air flow through the opening or openings to and from the user's nostrils along the posterior side 25 of shield 14. Such air circulation virtually eliminates moisture condensation and fogging.

Headband 12 evenly distributes the shield's very light load to the head and provides a strong support for shield 14 which minimizes fatigue.

It will be appreciated that face protector 10 has no frame and is attractive in appearance. It does not mess up a professional's hair. It is safe, trouble-free, and provides a completely new and unique approach to face shield design. It successfully accomplishes its objectives by virtue of its simplicity, flexibility, and versatility.

The absence of a frame makes face protector 10 very light, comfortable to wear, and relatively inexpensive to make, Shield 14 can be rapidly changed for easy cleaning, disinfection, and storage, It is easily trimmable with knife or scissors. It offers minimum interference with the operator, his instruments, and his patient.

Strips 20,22 allow versatility and adjustable anterior, posterior, and vertical positioning and repositioning of shield 14 to accommodate a wide range of user preferences, and allow changing shield 14 as many times as may be necessary without disruption to business.

What I claim is:

1. A comfortable to wear frameless face protector, comprising:
a transparent lightweight shield sufficiently flexible and deformable to easily match the shape of a user's head and to deflect upon accidental contact with a hard body;
a flexible, non-elastic headband for deftly and adjustably securing said shield to at least two positions on said headband; fastener means carried by said headband and by said shield for reusably and deftly attaching the opposite ends of said headband around the head of said user, and for reusably attaching the fastener means on said shield to said fastener means on said headband so as to establish a sufficiently large opening between said headband and said shield, whereby ample and unobstructed air circulation can take place through said opening to and from the nostrils of said user along the posterior side of said shield;
said headband being made of a woven absorbent material;
said fastener means including pairs of woven strips, one strip carrying woven hooks, and the other strip carrying woven loops;
said shield being suspended from said fastener means on said headband by the mechanical interaction between said hooks and loops, and said shield being positioned substantially parallel to the user's face; and
said fastener means on said shield and on said headband being easily deformable to adjust to the shape of the head of the user and to the shape of said shield.

2. A frameless face protector, comprising:
a readily-deformable ribbon;
first fastener means attached to the opposite ends of said ribbon for transforming said ribbon into an adjustable flexible headband around the fore, rear and sides of the head of a user;
second fastener means attached to at least two lateral positions on the exterior side of said ribbon intermediate said first fastener means;
a flat, transparent, thin shield made of plastic material and being readily deformable and flexible to easily match the face of said user;
third fastener means attached to at least two lateral positions on said shield and below the top edge thereof; and
said first, second, and third fastener means being readily deformable to match the shape of said shield and of the head of said user, thereby adjustably securing said third fastener means to said second fastener means, whereby said shield can assume different spaced relationships in horizontal and vertical directions relative to said headband.

3. The frameless face protector of claim 2, wherein said ribbon is flat, sweat-absorbing, and non-elastic 4. A frameless face protector, comprising:
a flat readily deformable ribbon made of a sweat-absorbing, non-elastic woven material;
first fastener means including a pair of fastener strips, each attached to an end of said ribbon for transforming said ribbon into an adjustable flexible headband around the fore, rear and sides of the head of a user;
second fastener means including a pair of fastener strips attached to at least two lateral positions on the exterior side of said ribbon intermediate said first fastener means;
a flat, transparent, thin shield made of plastic material and being readily deformable and flexible to easily match the face of said user and to deflect upon accidental contact with a hard body;

third fastener means including a pair of fastener strips attached to at least two lateral positions on said shield and below the top edge and near the corners thereof;

said first, second and third fastener means being readily deformable to match the shape of said shield and of the head of said user, and being readily compressible, thereby precluding concentrated pressure zones upon the user's head and face; and each pair of said fastener strips including one strip carrying woven hooks and the other strip carrying woven loops, whereby the loop strips become detachably fastened to the hook strips in whatever position they are pressed together, thereby adjustably securing said third fastener means to said second fastener means, whereby said shield can assume different spaced relationships to horizontal and vertical directions relative to said headband.

* * * * *